United States Patent [19]

Schreiber

[11] Patent Number: 5,142,043
[45] Date of Patent: Aug. 25, 1992

[54] PROCESS FOR PREPARING CEPHALEXIN MONOHYDRATE

[75] Inventor: Fred G. Schreiber, Highland Park, N.J.

[73] Assignee: Biocraft Laboratories, Inc., Fairlawn, N.J.

[21] Appl. No.: 521,831

[22] Filed: May 10, 1990

[51] Int. Cl.⁵ .......................................... C07D 501/04
[52] U.S. Cl. ..................................... 540/230; 540/228
[58] Field of Search ................................ 540/230, 228

[56] References Cited

U.S. PATENT DOCUMENTS

| | | | |
|---|---|---|---|
| 3,499,909 | 3/1970 | Weissenburger et al. | 260/306.7 |
| 3,694,437 | 9/1972 | Jackson | 260/243 C |
| 4,223,135 | 9/1980 | Walker et al. | 540/30 |
| 4,316,017 | 2/1982 | Walker et al. | 544/26 |
| 4,504,657 | 3/1985 | Bouzard et al. | 540/230 |

OTHER PUBLICATIONS

Bortesi et al., Preparation, Identification, and Quantitive NMR Determination of Silyl Derivatives of 6-Aminopenicillanic Acid, 7-Amino-3-Methyl-3-Cephem 4-Carboxylic and 7-Amino-3-Acetoxymethyl-3-Cephem-4-Carboxylic Acid, vol. 66, No. 12 (Dec. 1977) pp. 1767-1769.

Bruynes et al., Catalysts for Silylations with 1,1,1,3,3,3-Hexamethyldisilazane, American Chem. Soc. (1982).

Primary Examiner—Nicholas S. Rizzo

[57] ABSTRACT

Cephalexin monohydrate prepared by the silylation of 7-ADCA is obtained in high yield and of improved purity when the silylation step is carried out by refluxing in a solvent having a boiling point of over 100° C.

13 Claims, No Drawings

PROCESS FOR PREPARING CEPHALEXIN MONOHYDRATE

This invention relates to an improved method of preparing cephalexin monohydrate. More particularly, this invention method produces cephalexin monohydrate in high yield and high purity.

BACKGROUND OF THE INVENTION

It is known to prepare cephalexin monohydrate (VI) using as the starting material 7-aminodesacetoxycephalosporanic acid (hereinafter 7-ADCA) which has the formula (I)

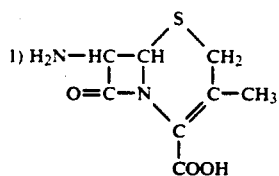

A silylation reaction is then carried out primarily to protect the carboxy group and incidentally to protect the free amine group to form an intermediate of the formula (II)

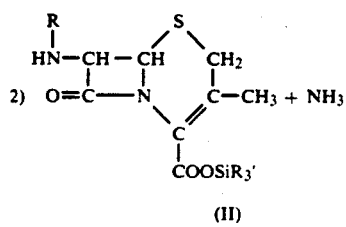

wherein R is hydrogen or $R'_3Si$ and R' is lower alkyl.

The silylation step has generally been carried out in solvents such as methylene chloride which has a boiling point of 40° C. at reflux, with various silylating agents in the presence of a catalyst such as saccharin. Room temperature reaction in acetonitrile has been disclosed in U.S. Pat. No. 3,694,437.

The silylated intermediate (II) is then reacted with a mixed anhydride. The mixed anhydride (IV) is made by converting D-(alpha)-phenylglycine Dane salt potassium ethyl ester (III) with pivaloyl chloride catalyzed with 2,6-lutidine in a suitable solvent.

The silylated product and the mixed anhydride are then combined in the cold to form an intermediate protected cephalexin (V) that is not isolated. This reaction is illustrated below:

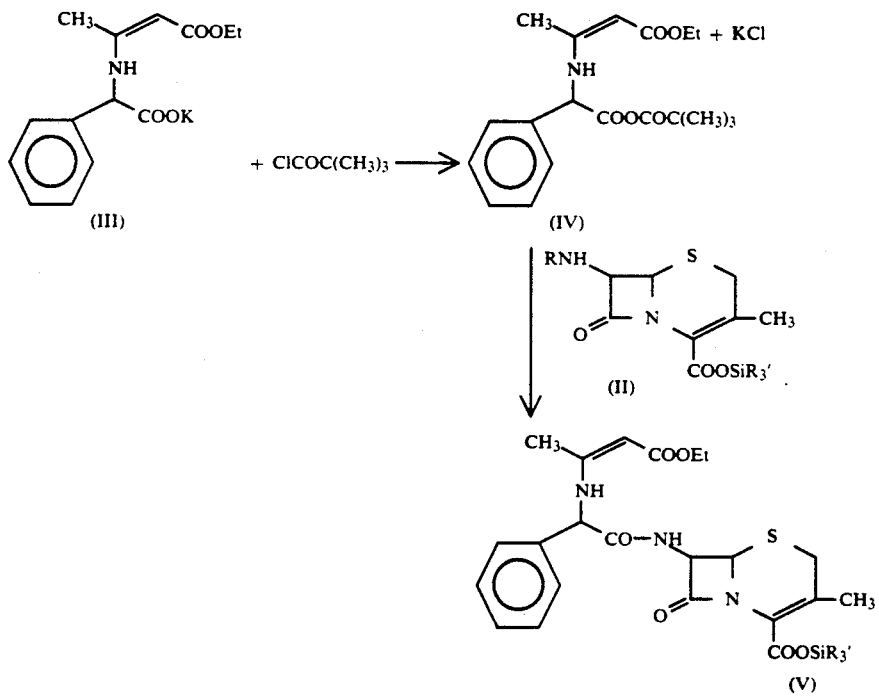

The product is then hydrolyzed to remove the silyl groups, forming cephalexin hydrochloride in solution. The hydrochloride is neutralized with a base in aqueous methanol to form the desired product, cephalexin monohydrate which has the formula (VI):

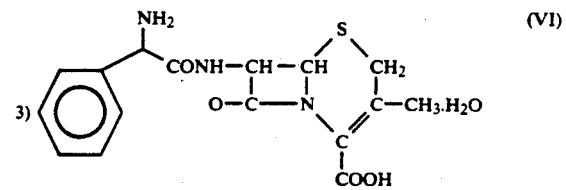

The above process always gives incomplete reaction of 7-ADCA to cephalexin. It has a yield that is lower than desired, e.g., in the range of about 70–75%. Low yields add to the cost of producing the product. The final product is sometimes contaminated with the 7-ADCA starting material. Attempts to improve the purity of the product by altering reaction conditions, such as time, temperature, concentration of reactants, ratios of starting materials and the like have had little effect on purity. Prevention of coprecipitation of 7-ADCA with the product is difficult because 7-ADCA tends to form as an amorphous material along with the crystalline product, if the pH of a solution of both is simply raised to the isoelectric point of cephalexin. A better crystallization is done by an awkward "simultaneous" method by feeding both the acidic product solution and a caustic solution into a reservoir at a pH of 6.5-7.0 to prevent coprecipitation of the 7-ADCA. This process is cumbersome at best.

Thus a method of improving the conversion of 7-ADCA in the above general process, but without sacrificing quality of the product or adding to existing costs, would be highly desirable.

SUMMARY OF THE INVENTION

I have found that improved conversion of 7-ADCA to cephalexin monohydrate can be obtained by substituting higher boiling solvents in the silylation step. Further, the presence of a catalyst such as saccharin is no longer required and can be eliminated. Still further, the product contains less 7-ADCA starting material than prior art processes and thus the final crystallization step is simplified.

DETAILED DESCRIPTION OF THE INVENTION

In the process of the invention, 7-ADCA and hexamethyldisilazane (HMDS) or other suitable silylating agents are reacted at reflux in a high boiling inert solvent, i.e., a solvent having a boiling point of over 100° C., to form a silylated product of the formula (II). Suitable solvents include toluene (b.p. 110.6° C. xylene (b.p. 138.4° C.). A catalyst such as saccharin is not required for the reaction at these temperatures.

Although the exact mechanism of this reaction is unknown, it is believed that complete or nearly complete conversion of 7-ADCA to cephalexin in higher boiling point solvents is due to one or both of the following occurrences in the silylation, neither of which occurs in lower boiling solvents: a) complete consumption of HMDS, and/or b) distillation of unreacted HMDS.

It is believed that unreacted HMDS, present in or added to a silylation solution, will quench the subsequent mixed anhydride, thereby preventing some of the silylated 7-ADCA from reacting properly. Bortesi et al, J. Pharm. Sci., 66(12), 1767 (1977) have reported that reaction of 7-ADCA with HMDS in higher boiling perchloroethylene will have a higher ratio of bis to mono-silylated 7-ADCA than when the same reaction is carried out in deuterochloroform. Since the amino group is less reactive than the carboxyl group, a higher temperature is needed to make the bis-derivative. Thus HMDS is more fully consumed at higher temperatures. However, too high a temperature, e.g. greater than 150° C., will lead to decomposition. On the other hand, too low a temperature will require a catalyst. For example, a silylation in toluene at only 90° C. would not proceed until saccharin was added.

It is also believed that the process is aided by high temperature distillation of part of the solvent from the silylation solution at temperatures greater than 100° C. In addition to expelling the ammonia by-product of the silylation, part of the toluene probably expels any unreacted HMDS. The same silylation and distillation as above, when carried out in methylene chloride, for example, repeatedly failed to remove unreacted HMDS.

Another benefit of using higher boiling solvents is the elimination of the need for a silylation catalyst, e.g. saccharin. Without a catalyst, silylation in methylene chloride proceeds very slowly, if at all.

A further benefit of using toluene or other high boiling solvent is a saving in material costs. A much higher concentration of 7-ADCA can be charged in toluene as compared to methylene chloride for example, with a concomitant higher concentration after distillation as well. A higher concentration of the mixed anhydride is present also, thereby using less solvent. The savings in solvent costs is more than one-half of the conventional method.

The resultant silylated product is then reacted with a mixed anhydride in known manner. Dane salt is reacted at low temperatures, between about −10° C. and about −30° C., with pivaloyl chloride in the presence of 2,6-lutidine in a solvent. The solvent can be the same solvent used for the silylation step for ease of recovery and recycling, but a lower boiling point solvent such as methylene chloride can also be employed.

However, when an aromatic solvent such as toluene is used for the mixed anhydride, a small amount of a polar aprotic solvent such as dimethylacetamide should be added to help dissolve the Dane salt and allow ready reaction with the acid chloride.

The mixed anhydride and the silylated product are combined in the cold to form a derivative (V) of cephalexin which is hydrolyzed, as with water and acid, to remove the silyl groups and form an aqueous solution of cephalexin hydrochloride.

This material is not isolated but is neutralized with hydroxide solution and crystallized directly from aqueous methanol to form the desired product, cephalexin monohydrate.

Alternatively, the cephalexin hydrochloride can be crystallized by the indirect, simultaneous method whereby the hydrochloride and hydroxide solutions are slowly added to a reservoir maintained at a pH of about 6.5 to 7.0 so as to maintain the pH and crystallize the cephalexin monohydrate.

The yields of the product are improved up to about 82-85%, and, more importantly, the purity of the product is improved by the process of the present invention. There is substantially less 7-ADCA contamination of the final product, regardless of the exact crystallization method employed. The product can be further purified of decomposition products and the like by treating with, for example, activated charcoal in known manner.

Another advantage of the present process is a simplified purification step. Heretofore in order to prevent large amounts of 7-ADCA from coprecipitating with the desired crystalline cephalexin monohydrate, the intermediate cephalexin hydrochloride and a caustic solution were added together to a reservoir maintained within the narrow pH range of 6.5 to 7.0. Thus the addition of the cephalexin hydrochloride and the caustic had to be carefully monitored to prevent the pH of the mixture from exceeding about 7.0, thereby causing alkaline decomposition, or below 6.5 to prevent coprecipitation of the 7-ADCA with the desired cephalexin monohydrate product.

Because there is far less 7-ADCA present in the present cephalexin hydrochloride solution of the present invention, the hydrochloride can be neutralized and the monohydrate product crystallized directly from solution without the need to use the "simultaneous" method.

The invention will be further illustrated by the following Examples, but the invention is not meant to be limited to the details described therein. In the Examples, parts are by volume and percent is by weight unless otherwise noted.

EXAMPLE 1

Part A. Silylation

A silylation mixture of 50 parts by weight of 7-ADCA, 200 parts of toluene and 40 parts of hexamethyldisilazane was refluxed for one hour. One hundred parts of distillate was collected. The solution was cooled to room temperature.

Part B. Preparation of the Mixed Anhydride

A mixture of 77.8 parts by weight of D-(alpha)-phenylglycine Dane salt potassium ethyl ester, 90 parts of toluene, 1.7 parts of 2,6-lutidine and 10 parts of dimethylacetamide was cooled to $-30°$ C. At this time 30.9 parts of pivaloyl chloride were added and the temperature was allowed to rise to about $-15°$ to $-10°$ C. and held there for 1.5 hours. The resultant anhydride mixture was then cooled to $-60°$ C.

PART C. Reaction of Products of Step A and Step B

The silylation product and mixed anhydride as obtained above were combined slowly over 30 minutes, allowing the temperature to increase to about $-40°$ C. to $-45°$ C. and maintained there for about 2 hours.

Part D. Hydrolysis

25 Parts of concentrated hydrochloric acid was added and then 200 parts of water. The temperature was held at $0°$ to $-5°$ C. for 0.5 hour and the mixture separated.

Part E. Simultaneous Crystallization

The aqueous layer was diluted with 125 parts of methanol. About 50 parts of this solution was added to a solution of 125 parts of water and 40 parts of methanol and the pH brought to 6.5 to 7.0 with 25% by weight sodium hydroxide solution. The mixture was seeded and stirred and crystallization began at $20°$ to $25°$ C. The remainder of the aqueous product solution was added dropwise to this slurry together with the sodium hydroxide so as to maintain the pH at 5.5 to 6.0. The final pH was 5.5.

Part F. Isolation of Cephalexin Monohydrate

The slurry was cooled to $0°$ to $5°$ C. and filtered. The filter cake was washed with 50 parts of 35% methanol at $0°$ C and then with 100 parts of acetone. The product was air dried overnight.

Cephalexin monohydrate was obtained in 82.9% yield (70.7 parts by weight) having the following analysis: Karl Fisher (KF) 5.5%; potency 991 microgram per milligram; 7-ADCA content below 0.1%; toluene 119 ppm.

EXAMPLE 2

The procedure of Example 1 Parts A-D was followed except using 1.5 times the quantities.

E. Direct Crystallization

The separated aqueous layer was diluted with 124 parts of methanol and 94 parts of water. The pH was increased to 3.0 at $22°$ C., the solution seeded and the pH slowly increased to 5.5 at $24°$ C., when the resultant slurry was cooled to $0°$ C.

The product slurry was filtered, the filter cake washed with 75 parts of $-15°$ C. methanol and then with acetone and dried overnight in air.

Cephalexin monohydrate was obtained in 81.4% yield (104.2 parts by weight) having the following analysis: KF 5.6%; potency 965 micrograms per milligram; 0.1% 7-ADCA; toluene 97 ppm.

COMPARATIVE EXAMPLE A

The procedure of Example 1 Part A was followed except substituting 200 parts of methylene chloride for toluene and adding 0.5 part by weight of saccharin catalyst. The product was refluxed for 2.5 hours, then stored overnight at room temperature under nitrogen.

Part B. Preparation of the Mixed Anhydride

The Dane salt, 236 parts of methylene chloride, 1.7 parts of 2,6-lutidine and 31.7 parts of pivaloyl chloride were combined. After cooling to 31 $10°$ to $-15°$ C. for 1.5 hours, 2.1 parts of 2-ethylhexanoic acid was added and the mixture was cooled to 31 $65°$ C.

Part C. Reaction of the Products of Step A and Step B

The silylation product was added to the mixed anhydride and the temperature held between $-35°$ to $-45°$ C. for 3.5 hours.

Part D. Hydrolysis

The mixture was hydrolyzed in 350 parts of water and 25.4 parts of 37% by weight hydrochloric acid and stirred for twenty minutes at $0°$ C., and then poured into a separatory funnel. The aqueous layer was treated with 2.5 parts of charcoal and filtered twice.

Part E. Formation of Cephalexin Monohydrate

The filtrate (492 parts) was diluted with 162 parts of methanol, the pH adjusted to 2.5 at $25°$ C. with 25% of sodium hydroxide, stirred for 0.5 hour and the amorphous 7-ADCA filtered off.

Part F. Direct Crystallization

The pH was increased to 3.0, mixed for 0.5 hour and brought to 4.5 at $20°$ C. The resultant slurry was cooled to $5°$ C. and filtered. The filter cake was washed with 100 parts of 30% aqueous methanol solution and 100 parts of acetone. The product was air dried overnight.

Cephalexin monohydrate was obtained in 76.9% yield (65.6 parts by weight).

Thin layer chromatogrphy showed the product was contaminated with 5-10% of 7-ADCA.

COMPARATIVE EXAMPLE B

Part A. Silylation 300 parts by weight of 7-ADCA, 183.5 parts by weight of HMDS and 3 parts by weight of saccharin were refluxed in 2127 parts of methylene chloride for 0.5 hour. 1200 Parts of solvent was distilled off and the solution cooled to $-5°$ C.

Part B. Prepartion of Mixed Anhydride

The mixed anhydride was made by dissolving 440.6 parts by weight of Dane salt potassium ethyl ester in 1350 parts of methylene chloride. 8.8 Parts by weight of 2,6-lutidine was added, the solution cooled to $-35°$ C.

and 171.3 parts by weight of pivaloyl chloride added. The temperature was held at −10 to −15° C. for 1.5 hours, when 10.8 parts by weight of ethylhexanoic acid was added. The solution was cooled to −80° C.

Part C. Reaction of Products of Step A and Step B

The silylation product as prepared above was added over 1.5 hours to the mixed anhydride solution, allowing the temperature to rise to from −40 to −30° C. over three hours.

Part D. Preparation of Cephalexin Hydrochloride

The mixture was quenched with 210 parts by weight of 31% hydrochloric acid and 1234 parts of water. The mixture was stirred for 20 minutes and the aqueous layer separated and filtered.

Part E. Simultaneous Crystallization

The filtrate was diluted with 500 parts of methanol and 200 parts of water. A crystallization sink was made with 240 parts of methanol and 750 parts of water. 299 Parts of the diluted filtrate was poured in, and the pH raised rapidly to 7.0 with 25% sodium hydroxide. The remaining product solution was added while maintaining the pH with sodium hydroxide solution between 6.6 and 7.0, except allowing it to drift to about 6.0 at the end.

The resultant slurry was cooled to 0° to 5° C. and centrifuged. The solid was washed with methanol and acetone and dried at 40° C.

Cephalexin monohydrate was obtained in 60.6% yield (310.2 parts by weight). The KF was 7.0% and 7-ADCA content was 2.4%.

I claim:

1. In a process for producing cephalexin monohydrate which comprises
    a) silylating 7-ADCA with a silylating agent in a solvent under reflex,
    b) reacting with a mixed anhydride in the cold,
    c) hydrolyzing to remove the sily groups,
    d) acidifying to form cephalexin hydrochloride in situ and
    e) neutralizing to precipitate cephalexin monohydrate, the improvement which comprises
        carrying out the silylation step in the presence of a solvent selected from the group consisting of toluene and xylene whereby the product is obtained high yield and high purity.

2. A process according to claim 1 wherein the silylation step is performed in the absence of a catalyst.

3. A process according to claim 1 wherein the solvent is toluene.

4. A process according to claim 1 wherein the solvent is xylene.

5. A process according to claim 1 wherein the silylating agent is hexamethyldisilazane.

6. A process according to claim 1 wherein the product is isolated by direct crystallization from aqueous methanol.

7. In a process for producing dephalexin monohydrate which comprises
    (a) silylating 7-ADCA with hexamethyldisilazane (HMDS) in a solvent under reflex,
    (b) reacting with a mixed anhydride in the cold,
    (c) hydrolyzing to remove the silyl groups,
    (d) acidifying to form cephalexin hydrochloride in situ and
    (e) neutralizing to precipitate cephalexin monohydrate, the improvement which comprises
        carrying out the silylation step in the absence of a catalyst and in the presence of a solvent selected from the group consisting of toluene and xylene at a temperature between 100° and 150° C., to produce cephalexin monohydrate in high yield and purity.

8. A process according to claim 7, wherein the solvent is toluene.

9. A process according to claim 8, wherein the product is isolated by direct crystallization from aqueous methanol.

10. A process according to claim 8, wherein the product is isolated by adding the cephalexin hydrochloride and a hydroxide solution to a reservoir maintained at a pH of about 6.5 to 7.0 so as to maintain the pH and crystallize the product.

11. A process according to claim 7, wherein the solvent is xylene.

12. A process according to claim 11, wherein the product is isolated by direct crystallization from aqueous methanol.

13. A process according to claim 11, wherein the product is isolated by adding the cephalexin hydrochloride and a hydroxide solution to a reservoir maintained at a pH of about 6.5 to 7.0 so as to maintain the pH and crystallize the product.

* * * * *

UNITED STATES PATENT AND TRADEMARK OFFICE
CERTIFICATE OF CORRECTION

PATENT NO. : 5,142,043

DATED : August 25, 1992

INVENTOR(S): FRED G. SCHREIBER

It is certified that error appears in the above-identified patent and that said Letters Patent is hereby corrected as shown below:

Column 2, line 55: Replace formula (VI) with the following formula

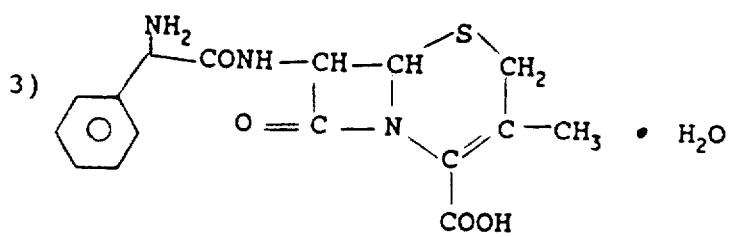

(VI)

Column 6, line 22: Change "31 10°" to -- -10°C--.

Column 6, line 24: Change "31 65°" to -- -65°--.

Column 7, line 40: Change "sily" to --silyl--.

Column 8, line 12: Change "dephalexin" to --cephalexin--.

UNITED STATES PATENT AND TRADEMARK OFFICE
CERTIFICATE OF CORRECTION

PATENT NO. : 5,142,043

DATED : August 25, 1992

INVENTOR(S) : Fred G. Schreiber

It is certified that error appears in the above-identified patent and that said Letters Patent is hereby corrected as shown below:

Column 8, line 15, Change "reflex" to --reflux--.

Signed and Sealed this

Twenty-first Day of September, 1993

*Attest:*

BRUCE LEHMAN

*Attesting Officer*      *Commissioner of Patents and Trademarks*